(12) United States Patent
Ugalde et al.

(10) Patent No.: US 7,541,447 B2
(45) Date of Patent: Jun. 2, 2009

(54) **PROCESS FOR THE PREPARATION OF AN IMPROVED *BRUCELLA* STRAIN PLASMID TO DEVELOP THE STRAIN AND THE VACCINE COMPRISING THE SAID STRAIN**

(76) Inventors: Juan Esteban Ugalde, Capdevila 2821, 9$^{no}$ piso depot. B Ciudad Autónoma, Bs. As., Capital Federal (AR); Diego José Comerci, Comlombres 243, 1$^{er}$ piso depot. 10 Ciudad Autónoma, Bs. As., Capital Federal (AR); Rodolfo Augusto Ugalde, Ortega y Gaset 1748, 4$^{to}$ piso Ciudad Autónoma, Bs. As., Capital Federal (AR); Vito G. Del Vecchio, 1935 N. Washington Ave., Scranton, PA (US) 18509

( * ) Notice: Subject to any disclaimer, the term of this patent is extended or adjusted under 35 U.S.C. 154(b) by 71 days.

(21) Appl. No.: 10/978,244

(22) Filed: Oct. 28, 2004

(65) Prior Publication Data

US 2006/0153868 A1     Jul. 13, 2006

(30) Foreign Application Priority Data

Sep. 28, 2004   (AR)  ............................. 20040103507

(51) Int. Cl.
*C07H 21/02*     (2006.01)
*C07H 21/04*     (2006.01)
*A61K 49/00*     (2006.01)
*A01N 63/00*     (2006.01)

(52) U.S. Cl. ..................... 536/23.1; 536/23.7; 536/24.1; 536/24.2; 536/24.3; 536/24.32; 424/9.1; 424/9.2; 424/93.1; 424/93.2; 424/93.4

(58) Field of Classification Search ................ 536/23.1, 536/23.7, 24.1, 24.2, 24.3, 24.32; 424/9.1, 424/9.2, 93.1, 93.2, 93.4
See application file for complete search history.

(56) References Cited

U.S. PATENT DOCUMENTS 5,718,903 A     2/1998   Adams et al.

OTHER PUBLICATIONS

Comerci et al; Vector Development for the Expression of Foreign Proteins in the Vaccine Strain *Brucella abortus* S19; Infection and Immunity; Aug. 1998; pp. 3862-3866; vol. 66, No. 8; American Society for Microbiology.
Cornish-Bowden, A; Nomenclature for Incompletely Specified Bases in Nucleic Acid Sequences: Recommendations 1984; Nucleic Acid Research; 1985; pp. 3021-3030;vol. 13-No. 9; IRL Press Limited; Oxford, England.

*Primary Examiner*—Rodney P. Swarts
(74) *Attorney, Agent, or Firm*—Gerry J. Elman; Elman Technology Law, P.C.

(57) ABSTRACT

A *Brucella* bacterium is modified by partial or complete deletion of the pgm gene, rendering the bacterium incapable of synthesizing a key enzyme in the metabolism of bacterial sugars. A live vaccine for immunization, prophylaxis or treatment of brucellosis comprises such a bacterium, either lyophilized or in a pharmaceutical vehicle. Nucleotide sequence fragments having the aforementioned deletion are disclosed, with methods for making them.

20 Claims, 8 Drawing Sheets

Fig. 2B

PROCESS FOR THE PREPARATION OF AN IMPROVED *BRUCELLA* STRAIN PLASMID TO DEVELOP THE STRAIN AND THE VACCINE COMPRISING THE SAID STRAIN

CROSS REFERENCE TO RELATED APPLICATIONS

This application claims priority pursuant to the Paris Convention from Argentina patent application 20040103507, filed Sep. 28, 2004, submitted herewith and incorporated herein by reference.

FIELD OF INVENTION

This invention belongs to the field of molecular biology/microbiology, in particular bacteriology. More specifically, this invention is related to the modification of a *Brucella* strain, the method used to develop it, and use of the modified strain to prepare a vaccine for the control of the disease brucellosis in mammals.

BACKGROUND

Brucellosis is a global zoonotic infection and contagious illness of worldwide distribution that affects a wide spectrum of mammals, from cetaceans and pinnipeds to domestic animals and humans. The illness is caused by a gram negative bacterium that belongs to the genus *Brucella* which is distinguished by seven species: *Brucella melitensis, B. abortus, B. suis, B. ovis, B. canis, B. neotomae* and *B. maris*. The genus is highly homogenous in that its genomic DNA is more than 95% homologous, prompting Verger et al. to propose to reclassify the seven *Brucella* species as a monospecific genus (Verger J. M., Grimont F., Grimont P. A. D. and Grayon M., *Brucella*, a monospecific genus as shown by deoxyribonucleic acid hybridization; Int. J. Syst. Bacteriol., 1985; 35:292-5). This proposal has not yet been formally adopted. The nomenclature based on the seven species described earlier is of use because it takes into consideration the culture, host range, and epidemiological characteristics of each species.

Human brucellosis is a serious and debilitating illness, characterized by diverse clinical manifestations such as undulating fever, osteoarticular complications, endocarditis and neurological disorders. The primary pathological symptoms of the disease in cattle, goat, and sheep are abortion in pregnant females and sterility in males, due to the fact that the *Brucella* cells colonize the placenta, fetal tissue and reproductive organs.

*Brucella* is an intracellular pathogen, capable of actively invading and multiplying inside the phagocytotic cells of the host organism, mainly polymorphonuclear leukocytes (PMN) and macrophages. The *Brucella* exploits the phagocytic cells for transport to lymphatic tissue, uterus, and the placenta. PMN's and the macrophages fail to eliminate the bacteria from the primary site of the infection. Since the *Brucella* have no standard pathogenicity determinant, the exact mechanism of infection for these bacteria has not been defined.

The elimination of *Brucella* in the infected animal requires the generation of a cellular immune response. In vitro studies and experiments of passive transference indicate that antibodies are also involved in immune protection, especially antibodies specific to the O chain of the lipopolysaccharide (LPS).

The incidence and prevalence of brucellosis varies widely from country to country, but it can be affirmed that bovine brucellosis, caused mainly by *B. abortus*, is the most disperse form and is responsible for the largest economic loss (Corbel M. J., Brucellosis: an overview; Em. Inf. Dis., 1997; 3:213-21). The principal source of infection in humans is the consumption of contaminated food, especially unpasteurized milk products and contact with infected animals. Thus, prevention of human brucellosis is dependent on the control of the disease in animals.

Countries with large cattle populations employ the naturally attenuated *B. abortus* S-19 strain vaccine to control bovine infection. This strain is genetically stable; however, the reason for its attenuation remains unknown. The principal characteristic of this vaccine strain is its low level of pathogenicity and its elevated level of conferred protection, especially its anti-abortion effects, when the proper administration method and dosage are followed. However, the S-19 strain offers some disadvantages which include: (1) it has an elevated persistence when it is inoculated into adult animals; (2) when administered intravenously or in elevated dosages to pregnant animals it can cause abortion; (3) it is pathogenic to humans and (4) serological diagnosis is complicated because it generates agglutinating antibodies indistinguishable from those generated by pathogenic field strains. This last characteristic is due to the fact that the lipopolysaccharide of the S-19 strain, *Brucella*'s immunodominant antigen, is identical to that of the pathogenic field strains.

Various alternatives to circumvent the disadvantages of the S-19 strain have been explored. Immunologic tests capable of discriminating between antibody titers of infected and vaccinated animals have been described. Strains that lack surface layer LPS, commonly termed as rough, have been developed. One of these strains, the mutant, rough RB51, is attenuated and incapable of producing agglutinant antibodies against LPS in the host. G. G. Schurig, et al., Biological Properties of RB51: a stable rough strain of *Brucella abortus*. Vet. Microbiol. 28:171-188 (1991).

The RB51 strain was derived from the pathogenic *B. abortus* 2308 strain by successive passages in media containing streptomycin. The genomic cause of the RB51 phenotype remains unknown. Experimental inoculations in animals demonstrated that RB51 does not interfere with serological diagnostics but the protective immunity conferred is significant but not superior to that generated by the S-19 strain. This strain was recently licensed for use in bovines.

U.S. Pat. No. 5,718,903 describes a *B. abortus* 2308 m106R:Tn5lacZ vaccine strain that can differentiate vaccinated from infected animals. This is a stable mutant strain that was generated by a genomic transposition which resulted in the lack of the O-antigen and which conferred protective immunity against wild *B. abortus* pathogenic strains.

Thus, there is a need for a *Brucella* vaccine that can offer superior protective immunity against brucellosis, does not interfere with the serological diagnostics of the illness, and lacks the disadvantages of the strains presently in use.

SUMMARY OF THE INVENTION

The present invention provides a method for obtaining new attenuated and protective *Brucella* strains, especially *B. abortus*. This is accomplished by a selective mutational deletion of the pgm gene that is responsible for the synthesis of the phosphoglucomutase protein, a key enzyme in the metabolism of bacterial sugars. Phosphoglucomutase catalyzes the formation of glucose-1-phosphate from glucose-6-phosphate. Glucose-1-phosphate is the donor of glucose for the synthesis of UDP-glucose which in turn is the donor of glucose for the synthesis of the LPS core and other polysaccharides. The lack of this enzyme impedes the production of glucose-1-phosphate which is the intermediary in a series of anabolic reactions that lead to the synthesis of LPS and cyclic glucan, molecules that participate in the virulence of *Brucella*. The loss of these molecules results in the nonvirulence of this strain. This strain confers superior protective immunity when compared to presently used vaccine strains.

The present invention also provides a method to prepare a plasmid which contains the dicistronic SacB-Gm utilized in the described method. The plasmid identified is pSG75.

Yet another aspect of the present invention relates to the plasmid obtained through steps of the method described which contains the dicistronic cassette SacB-Gm. The plasmid identified is pSG75.

The invention also refers to vaccines against *Brucella* which contain a mutant strain that lacks the O-antigen of the lipopolysaccharide in a pharmaceutically acceptable vehicle. These are vaccines of rough, attenuated strains, which offer protection against wild type pathogenic *Brucella* strains, especially against *B. abortus*.

The present invention includes the development of a mutant strain which lacks the O-antigen of the lipopolysaccharide (LPS) which can serve as a vaccine against brucellosis in mammals, including man. It offers protection against wild type pathogenic *Brucella* strains, particularly against *B. abortus*. Experimental inoculations in animals demonstrate that the vaccine strain is rapidly eliminated from the animal yet is capable of generating a protective immunity when the animal is challenged with the pathogenic strain.

BRIEF DESCRIPTION OF THE DRAWINGS

FIGS. 2A and 2B are the two parts of a step diagram on the development of the Δpgm strain of *B. abortus* utilizing the dicistronic SacB-Gm.

BRIEF DESCRIPTION OF THE SEQUENCE CLASS TYPES

Figure 1:
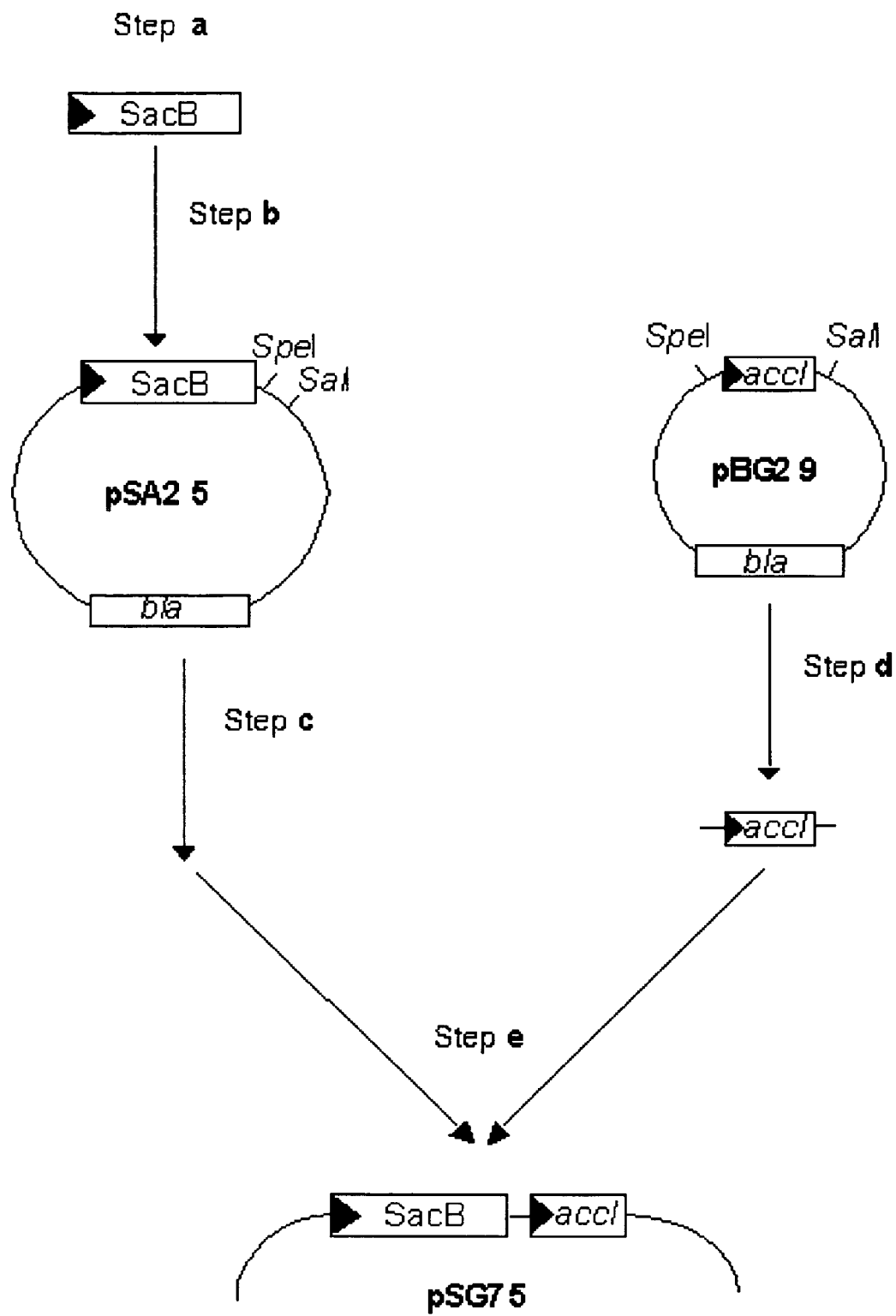
FIG. 1 is a step diagram of the construction of the dicistronic SacB-Gm plasmid (pSG75).

The following sequence descriptions and sequence lists are part of this application:

SEQ ID NO. 1: is the complete nucleotide sequences of the dicistronic pSacB-Gm vector used to make an effective deletion of the pgm gene. The sequence of the SacB vector can be observed (from the base 61 to 1577, in bold letters); the sequence of the site recognized by the restriction enzyme SpeI (from the base 1582 to 1587, in bold and underlined letters); the sequence of the Gm vector (from the base 1588 until 2354, underlined) and the sequence of the site recognized by the restriction enzyme SalI (from the base 2394 to 2399, in bold, italicized and underlined letters).

SEQ ID NO. 2: is the nucleotide sequence of the pgm gene of *B. abortus* 2308. This gene was deleted from *B. abortus* 2308 strain and is the objective of the method proposed herein. The codifying sequence of the pgm gene can be observed (from the base 104 until 1728, in bold letters) and the sequence of the site recognized by the restriction enzyme HindIII used to delete the region between both of the restriction sites (from the base 308 until 313 and from the base 1399 until 1405, in bold and underlined letters).

SEQ ID NO. 3: is the nucleotide sequence of the pgm gene of *B. suis* 1330. Its elimination from the genome of the pathogenic strain is the objective of the method disclosed herein. The codifying sequence of the pgm gene can be observed (from the base 1, or initiation code, until 1631, or finalization code, in bold letters) and the sequence between the two sites for a restriction enzyme, preferably HindIII, employed to delete the zone between both of the restriction sites (from the base 205 until 210, and from the base 1303 until 1308, in bold letters and underlined).

SEQ ID NO.4: is the nucleotide sequence of the pgm gene of *B. melitensis* 16-M. Its elimination from the genome of the pathogenic strain is the objective of the method disclosed herein. The codifying sequence of the pgm gene can be observed (from the base 1, or initiation code, until 1630, or finalization code, in bold letters) and the sequence between the two sites for a restriction enzyme, preferably HindIII, employed to delete the zone between both of the restriction sites (from the base 205 until 210, and from the base 1302 until 1307, in bold letters and underlined).

The sequence lists employ the code of one letter for the characters of nucleotide sequences, in conformance with the standards of the IUPAC-IUBMB described in *Nucleic Acids Research* 13:3021-3030 (1985)

DETAILED DESCRIPTION

Terminology

The meaning for all scientific and technical terminology utilized in this application are those commonly used in the field, unless an alternate meaning is specified.

In the present application the term "dicistronic" is used to signify the transcriptional unit composed of the accl and sacB genes.

The term "dicistronic cassette" is used to signify the genetic cassette composed of the transcriptional unit accl-sacB.

The term "mutation" is used to signify a change in the nucleotide sequence or in the aminoacids of a protein.

The term "b/a" refers to the gene which has antibiotic resistance to ampicillin.

The term "accl" refers to the gene which has antibiotic resistance to gentamicin.

Term "sacB" refers to the gene which codifies the levansucrase of *Bacillus subtilis*. This gene, when expressed in gram negative bacteria, generates an inability to grow in cultures that contain 10% sucrose.

The term "SpeI" refers to a restriction enzyme.

The term "SalI" refers to a restriction enzyme.

The term "pSA25" refers to the plasmid that contains the sacB gene, cloned in the vector PGEMT-easy.

The term "pBG29" refers to the plasmid that contains the accl gene, cloned in the vector pBluescript KSII at the restriction site BamHI.

The term "pSG75" refers to the plasmid which contains the dicistronic cassette SacB-Gm in the vector PGEMT-easy.

The term "Kan" refers to the gene which has antibiotic resistance to kanamycin.

Term "pgm" refers to the gene which codifies the phosphoglucomutase enzyme of *Brucella abortus*.

The term "EcoRV" refers to a restriction enzyme.

The term "SphI" refers to a restriction enzyme.

The term "SacI" refers to a restriction enzyme.

The term "HindIII" refers to a restriction enzyme.

The term "pUB22" refers to a fragment of approximately 4300 bp of the *Brucella abortus* genome which contains the pgm gene which codifies the cloned phosphoglucomutase at EcoRI restriction site of vector pUC19. Vector pUC19 is not replicated in *B. abortus*, behaving like a suicide vector.

The term "pUB22::SG" refers to the pUB22 plasmid which possesses, inserted at the restriction site EcoRV, the dicistronic cassette SacB-Gm. Said cassette is inserted in the pgm gene.

The term "pKB43" refers to a fragment of approximately 4300 bp of the *Brucella abortus* genome which contains the pgm gene which codifies the cloned phosphoglucomutase at the restriction site EcoRI of vector pK18 mob. Vector pK18 mob is not replicated in *B. abortus*, but it is conjugative.

The term "pKB43Δpgm" refers to the plasmid pKB43 digested with HindIII, purified and re-ligated. This is the way to obtain the pgm gene deleted in great part, cloned in a suicide vector in *B. abortus*, and conjugative.

The term "effective quantity" refers to a quantity of protective strain present in a vaccine that is sufficient to produce a protective effect against challenges from a wild *Brucella* strain that produces the disorders previously described in the treated animal.

By "pharmaceutically acceptable" reference is made to the inclusion of any agent that does not interfere with the efficiency of the biological activity of the strain that provides immunity and at the same time does not result in toxicity to the human or animal patient that incorporates it into its organism.

"Δpgm complemented strain" or "Δpgm (pBBE30)" refers to the Δpgm strain, the genome of which has been complimented by way of introduction of the pBBE30 plasmid inside the cell, said plasmid contains the genetic code of the pgm gene. Obtaining the Δpgm strain For the development of this new vaccine strain, the process of deletion of 60% of the pgm gene which codes for the phosphoglucomutase enzyme in the gram negative bacterium strain *Brucella*, was performed. To achieve this goal, the codifying gene was cloned and sequenced. Using genetic engineering techniques, the following steps were followed to obtain the deletion.

Construction of the Dicistronic SacB-Gm (Plasmid pSG75)

To generate a deletion of the pgm gene in *Brucella*, the plasmid vector pSG75 was developed. The vector possesses the accl gene that confers resistance to gentamicin, cloned together with the SacB gene that codifies for the levansucrase. The SacB gene, when expressed in Gram negative bacteria such as *Brucella*, has a lethal effect on the bacteria if it is cultivated in a medium containing sucrose. This characteristic makes it useful for use as a marker of counter-selection.

The vector, denominated pSG75, permits obtaining deletions of the desired gene in two steps, transformation/recombination and selection. During the first event of transformation/recombination, an insertion of the dicistronic SacB-Gm in the pgm gene is generated. In the process of selection, the colonies resistant to gentamicin that acquire the dicistronic SacB-Gm are obtained. These colonies are also sensitive to 10% sucrose and cannot grow in a medium that contains it.

During the second round of transformation/recombination, the exchange of the SacB-Gm markers for the deleted allele, pgm is produced. In this round of selection, the resistant colonies that lack a medium containing 10% sucrose are obtained. These are the colonies that effectively exchanged the selection and counter-selection markers for the pgm gene deleted at 60%.

The system is relatively simple to manipulate, it is low in cost and applicable to any gram negative bacteria.

Procedure for Obtaining pSG75 Containing SacB-Gm Dicistronic Cassette

The procedure for obtaining the pSG75 plasmid by employing standard techniques is described in molecular biology laboratory manuals such as the Sambrook et al. (1989) reference cited hereinbelow. The procedure has the following steps:

A) Using PCR, the SacB gene is amplified through the pUM24 plasmid. The amplified region is the one that bears the codifying SacB sequence without the regulatory sequences.

B) The PCR product of the SacB amplification is then cloned in the plasmid vector PGEMT-Easy (Promega Corporation), thereby the pSA25 vector is generated.

C) Vector pSA25 is digested with restriction enzymes, preferably SpeI and SalI. The digested vector is treated with alkaline phosphatase, according to manufacturer's specifications.

D) The accl gene of the pBG29 plasmid is digested using the restriction enzymes, preferably SpeI and SalI. The fragment corresponding to the accl gene is purified after separation on 1% agarose gel. And in the final step:

E) The DNA fragment corresponding to the accl gene is ligated to the pSA25 plasmid previously digested with SpeI and SalI, using an enzyme DNA ligase. This way, plasmid pSG75 containing the SacB-Gm dicistronic cassette is obtained.

Construction of the Δpgm Strain

To construct a deletion in the pgm gene of *Brucella*, an insertion of the accl marker gene for selection and SacB for counter-selection (present in the dicistronic cassette SacB-Gm) is made. Once the strain with the pgm gene interrupted by the dicistronic SacB-Gm, is generated, the markers are replaced by a deleted copy of the pgm gene by restriction digestion.

The procedure is detailed as follows:

A) Prepare the plasmid pSG75 which contains the dicistronic genetic construction SacB-GmB) Prepare the plasmid pUB22 which contains the pgm gene of *Brucella abortus*.

C) Prepare the pUB22::S-G plasmid containing the pgm gene of *Brucella abortus* interrupted with the dicistronic SacB-Gm.

D) Introduce the pUB22::S-G plasmid into a pathogenic strain using electroporation.

E) Select an intermediary *Brucella* strain, which contains the pgm gene interrupted by the dicistronic cassette SacB-Gm.

F) Obtain the pKB43Δpgm which contains a deletion of the order of 60% of the pgm gene and introduce it in the *E. coli* S17.1λpir strain.

G) Select a *Brucella* strain Δpgm which contains a deletion in the order of 60% of the pgm gene.

H) Verify that the *Brucella* Δpgm strain generated in step G lacks phosphoglucomutase activity as well as other derived properties that depend on the same gene.

Completion of Preparation of New Δpgm Strain

The procedure is detailed as follows:

A) The method follows the steps A), B), C), D) and E) as above corresponding to the procedure for obtaining the pSG75 plasmid which contains the dicistronic cassette SacB-Gm.

The plasmid pSG75 containing the dicistronic SacB-Gm is digested with restriction enzymes, preferably SphI and SacI. The protruding ends are transformed into blunt ends by the action of a DNA polymerase, preferably a T4 DNA polymerase, according to the standard procedure recommended by the manufacturer. The digested product is submitted to electrophoresis on 0.8% agarose gel. The DNA fragment, 23877 bp long, corresponding to the SacB and accl genes, is purified from the gel.

B) The pUB22 plasmid, containing the pgm gene of a *Brucella* strain, is digested with EcoRV and is treated with an alkaline phosphatase following the instructions provided by the manufacturer. The digested product is submitted to electrophoresis on 0.8% agarose gel and the DNA fragment corresponding to the traced plasmid is purified from the gel.

C) The traced pUB22 plasmid and the DNA fragments that contain the dicistronic SacB-Gm are ligated using a DNA ligase enzyme, preferably T4 DNA ligase, according to standard procedure. The resulting mixture is used to transform an *E. coli* strain, preferably DH5αF'I$^q$. The transformed colonies are then amplified and the resulting pUB22::S-G plasmid is purified.

D) The pUB22::S-G plasmid is introduced into a *Brucella* strain, which is selected from the group consisting of *B. melitensis, B. abortus, B. suis, B. ovis, B. canis, B. neotomae* and *B. maris*. Preferably a *B. abortus* strain is used, even more preferably a *B. abortus* 2308 strain is used. The strain is introduced using electroporation according to standard techniques. The Brucellae are then cultivated in a medium supplemented with gentamicin, preferably the medium used is TSB ("Triptic Soy Broth") supplemented with gentamicin, in order to select the cells that received the construct.

Colonies resistant to gentamicin are assayed in a medium supplemented with ampicillin, preferably the medium used is TSB supplemented with ampicillin. The colonies sensitive to ampicillin, which are probable candidates to have recombined the pgm gene with the copy interrupted by the dicistronic SacB-Gm, are streaked for posterior analysis of their sensitivity to sucrose, preferably with a concentration of 10%. Colonies sensitive to sucrose are streaked for further genetic analysis using standard techniques known in the field, such as: Polymerase Chain Reaction (PCR), Southern Blot, etc.

Figure 2A:
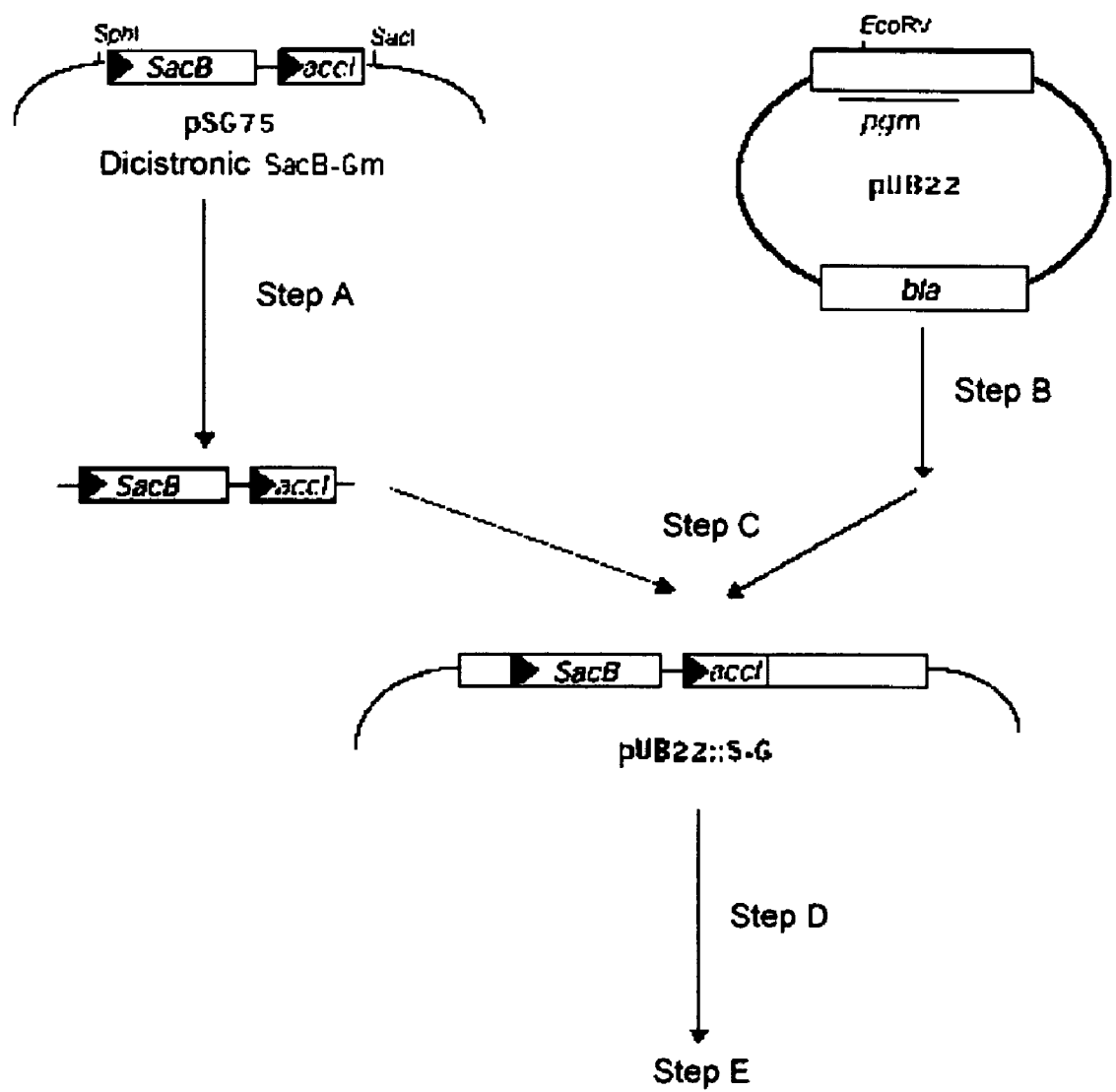
Figure 2B:
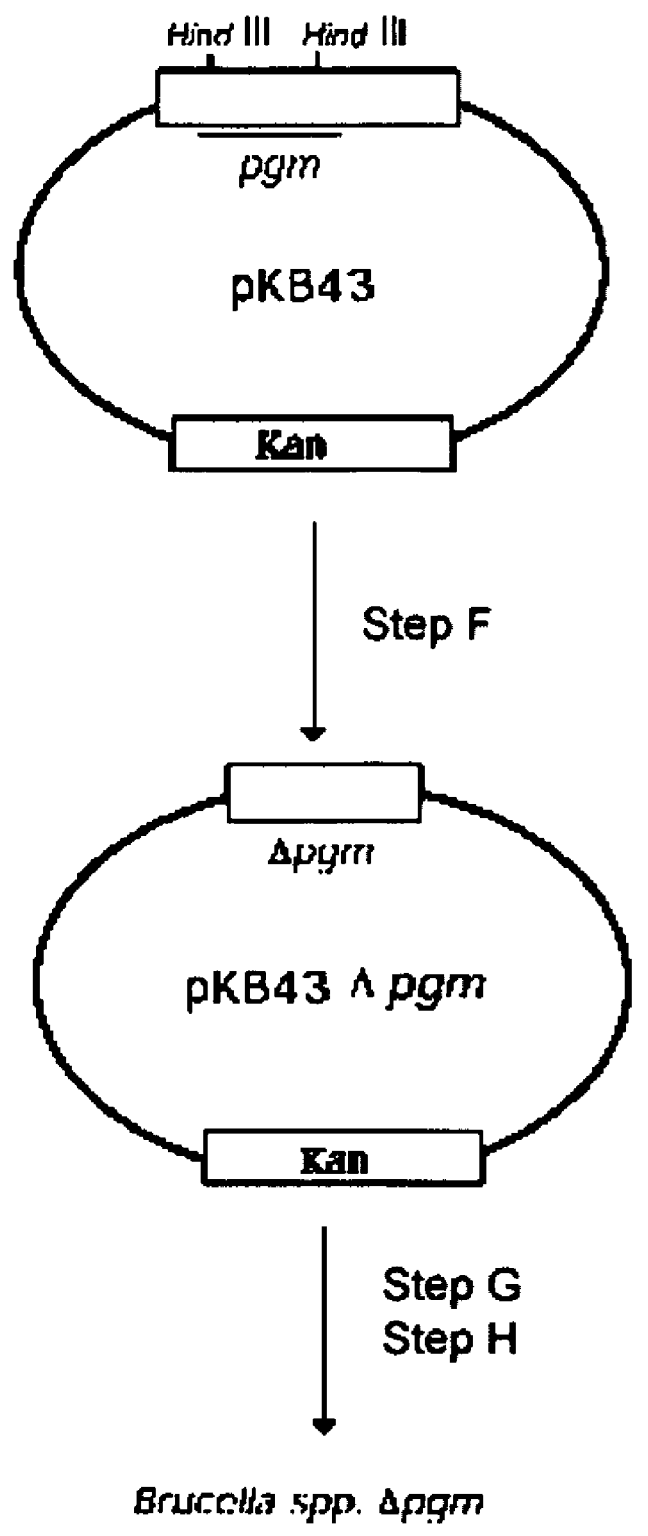

By this procedure an intermediary *Brucella* strain is generated, preferably, from *B. abortus* 2308 from which *B. abortus* A1 was obtained, containing the pgm gene interrupted with the SacB-Gm dicistronic cassette, as indicated in FIGS. 2A and 2B.

E) To generate the deletion of the pgm gene, the pKB43 plasmid is digested with HindIII restriction enzyme, according to standard procedure. The digested product is separated on 0.8% agarose gel and the corresponding fragment of the pgm gene which lacks the central region of 1100 bp (equivalent to 67% of the gene) is purified. The plasmid is re-ligated to generate the plasmid pKB43Δpgm.

The pKB43Δpgm plasmid is introduced in an *E. Coli* strain, preferably using the *E. coli* S17.1λpir strain, and is conjugated to the intermediary *Brucella* strain, which, for example, in *B. abortus* is *B. abortus* A1. The ex-conjugates are selected in a medium supplemented with 10% sucrose, preferably TSB supplemented with 10% sucrose, and nalidixic acid. Colonies resistant to sucrose are assayed for their sensitivity to gentamicin and kanamycin.

F) The obtained colonies Sac$^R$, Gm$^S$ and Kan$^S$ are analyzed using PCR and Southern Blot standard techniques to confirm the replacement of the markers SacB-Gm by the deleted copy of the pgm gene.

And, in the final step:

G) The new strain generated, preferably denominated "*Brucella* Δpgm strain", depending on the *Brucella* strain employed, will be *B. melitensis* Δpgm, *B. abortus* Δpgm, *B. suis* Δpgm, *B. ovis* Δpgm, *B. canis* Δpgm, *B. neotomae* Δpgm and *B. maris* Δpgm. It is preferred that a *B. abortus* strain be used, and then *B. abortus* Δpgm is obtained. The *Brucella* Δpgm strain is desirably assayed using biochemical and biological tests to confirm the absence of phosphoglucomutase activity and other properties derived that are dependent on the same.

An example of such a new strain, *B. abortus* Δpgm, was characterized using biochemistry. This Δpgm strain lacks the O-antigen and thus its LPS is incomplete, possessing the lipid A and having an incomplete LPS core.

*Brucella*'s Antigenic Label

*Brucella* Δpgm's vaccine strains can be bound to the antigenic label. This labeling consists of introducing an expression vector specifically designed for use in *Brucella*. This vector has a promoter, regulatory sequences and secretion signals exclusive to the *Brucella* species. Additional multi-cloned sites to allow the expression of the desired antigenic label are described by Comerci et al. (Comerci D. J., Pollevick G. D., Vigliocco A. M., Frasch A. C. C. and Ugalde R. A.; "Vector Development for the Expression of Foreign Proteins in the Vaccine Strain *Brucella abortus* S19"; *Infection and Immunity*, 1998. 66: 3862-3866).

For an antigenic label, it is particularly proposed, to use highly antigenic repetitive antigens. These are excellent candidates for use as an antigenic label since they are relatively easy to express in a recombinant form and in quantities compatible with generating a specific immune response. Also, its expression in Brucella does not alter the culture characteristics of the same, nor does it change its attenuation, or immunological and protective efficacy.

Use of this vaccine strain, which wears a distinct antigenic label, permits a quick and specific differentiation between the vaccinated and infected animals, by using ELISA. Also, it is possible to implement a quick diagnosis based on the use of reactive strips such as those frequently used in pregnancy tests.

Use of the labeled vaccine against Brucella not only can be useful to discriminate vaccinated animals, but it can also be a very useful as a sanitary tool, for example in the implementation of a large scale vaccine campaign. Inclusion of different synthetic, antigenic repetitions can be useful to differentiate vaccinated animals from different geographic regions, having had different vaccination periods, or to label products from different companies.

Intracellular Multiplication Capacity

Figure 3:
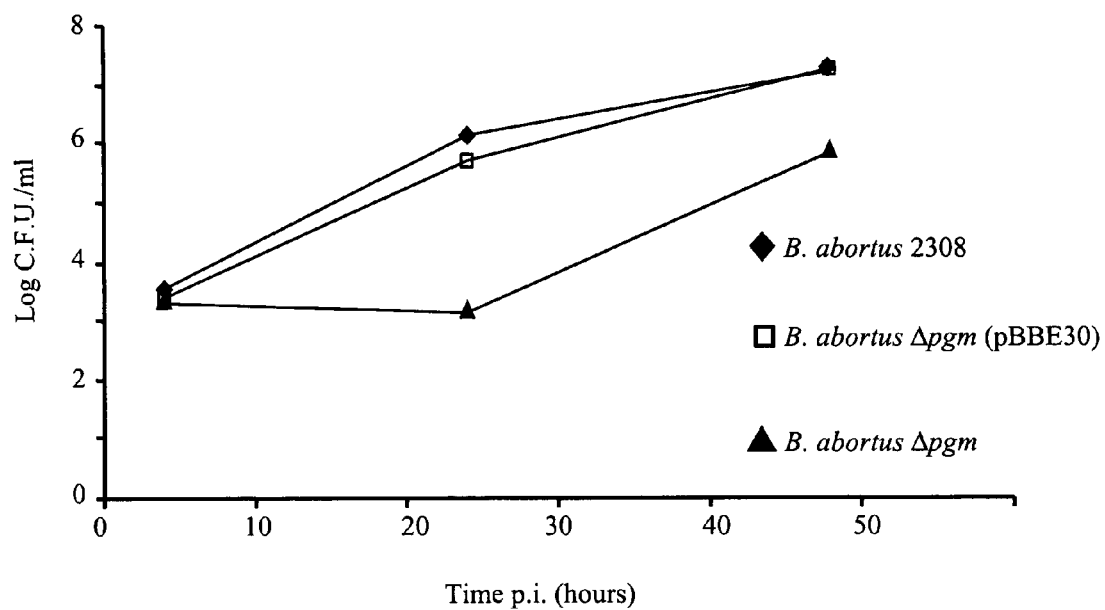
FIG. 3 is a line graph of an experiment that compares the intra-cellular replication of the Δpgm strain and pathogenic 2308 strain.

B. abortus Δpgm strain's capacity to replicate itself in human epithelial cells is assayed using HeLa cell line. To achieve that goal, a single layer of HeLa cells are infected with $10^5$ CFU (colony-forming units) with an infection multiplicity of 500:1, in other words 500 bacteria of the mutant to 1 HeLa cell. The culture was washed to eliminate the bacteria that had not entered the cells and HeLa cells were lysed at different times of post-infection and the intracellular bacteria were determined. As FIG. 3 illustrates, the Δpgm strain possesses a slower kinetic of replication than that observed with the wild 2308 strain. Despite this delay at the beginning of replication, the mutant is capable of replication reaching values of $10^6$ CFU/cm$^3$.

Attenuation Study in an Animal Model

Figure 4:
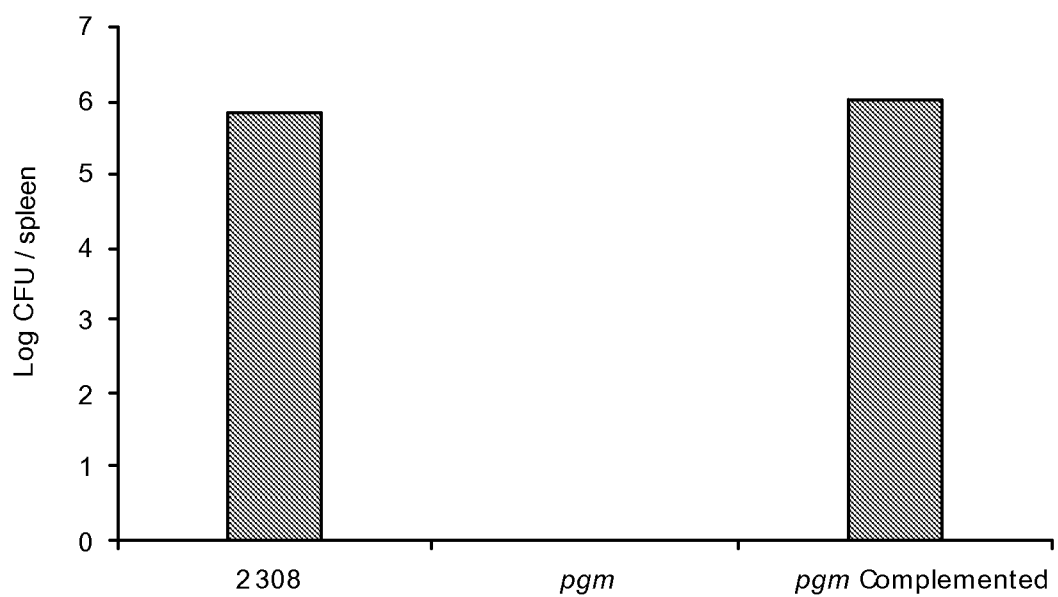
FIG. 4 is a bar graph of an experimental comparison of the persistence of the Δpgm strain and the pathogenic 2308 strain in mice spleens.

B. abortus Δpgm strain virulence was assayed in mice. Towards that end, $10^5$ CFU of the wild 2308 strain and of the mutant strain were injected intraperitoneally in five, 6 week-old female BalbC mice. Fifteen days post-inoculation the mice were sacrificed and their spleens were removed to count the viable bacteria. FIG. 4 shows the obtained results. One can observe that while in mice injected with the wild type strain $10^6$ CFU are found per spleen, those injected with the Δpgm strain have no viable bacteria, which indicates that the strain has been completely eliminated from the mouse. This result demonstrates that the Δpgm strain is non-virulent for mice.

Figure 5:
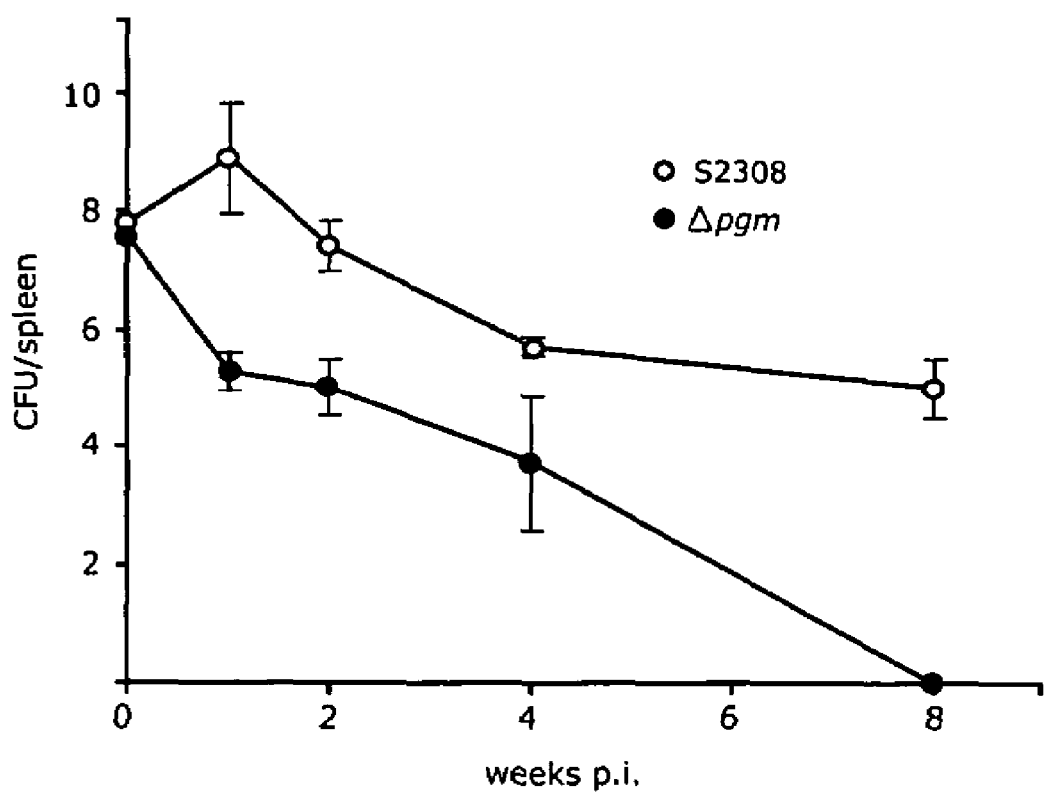
FIG. 5 is a line graph that represents results obtained when mice were inoculated with $10^7$ CFU (colony forming unit) of the wild strain 2308 and with the Δpgm strain.

Even at high dosages such as $10^7$ CFU, the number of viable bacteria of the Δpgm strain recovered from the spleens was, in all of the time intervals tested, significantly less than those of the virulent 2308 parent strain. After eight (8) weeks post-inoculation, Δpgm was completely eliminated from the inoculated mice, which indicates a severe virulence reduction, even at high dosages. FIG. 5 represents the results obtained for this mice virulence assay. The mice were inoculated with $10^7$ CFU of the wild strain 2308 or Δpgm. The number of viable bacteria recovered from the spleen was determined at the indicated times and the bars represent the average ± standard deviation.

Antibody Response Against the O-Antigen

LPS serologic response against the O-antigen was analyzed in mice inoculated with the Δpgm and compared against that generated by the virulent parent strain 2308. The presence of antibodies specific for O-chain of the LPS in the sera, was analyzed using an FPA assay using as a tracer O-antigen purified from B. abortus 2308 and conjugated to fluorescein-5-isothiocyanate (FITC). This technique is the most sensitive and precise of all those available in the brucellosis field.

Figure 6:
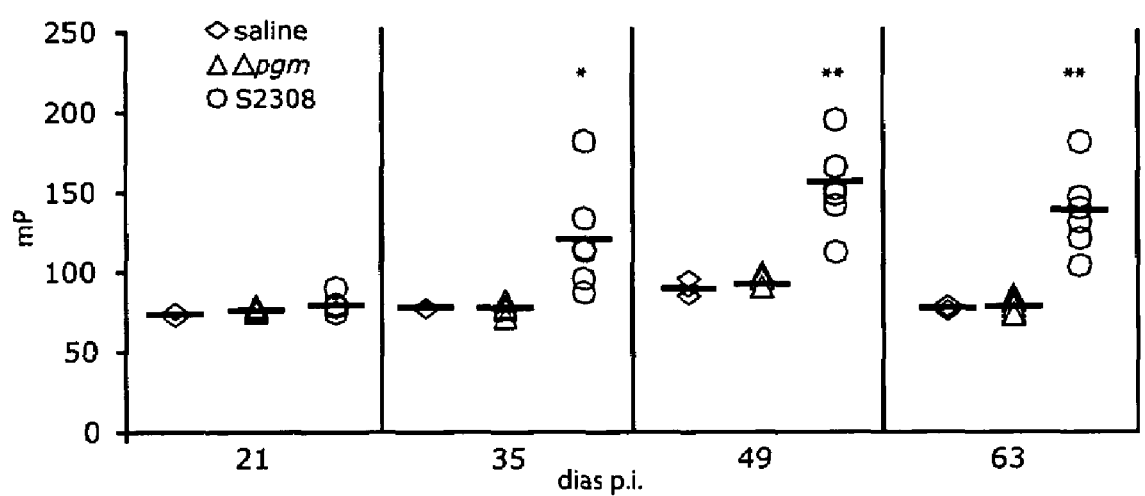
FIG. 6 is a plot of data representing results obtained in an anti-O antibody detection assay. Groups of six (6) mice were inoculated with $5\times10^5$ CFU of each strain and saline as control and their sera was obtained at the indicated times. Antibodies specific to the O chain of the LPS were determined by a fluorescence polarization assay (FPA). The horizontal bars represent the average value of the group. *$P<0.01$, **$P<0.001$ compared to the control group inoculated with strain S2308.

The mice that received the B. abortus 2308 strain generated O-antibodies the maximum titer of which was observed at 49 days post-inoculation (152.71±27.65 mP) (FIG. 6). On the other hand, the mice that received the Δpgm strain as well as the mice in the control group inoculated with a physiologic solution, were incapable of generating O-antibodies in all intervals of times tested (92.33±3.66 mP and 92.20±7.10 mP respectively at 49 days post-inoculation). These results indicate that the Δpgm strain is incapable of generating a humoral response against LPS' O-antigen.

The presence of agglutinating antibodies was investigated analyzing the same sera through an agglutination assay in platelet with buffered antigen (BPAT). The sera of mice inoculated with B. abortus 2308 generated a rapid and intense agglutination in a 1:25 and 1:250 dilution. Instead, the sera of mice inoculated with Δpgm did not present agglutination in any of the dilutions tested. This result indicates that the Δpgm is also incapable of generating agglutinating antibodies due to the lack of LPS' O-chain.

Generating an Immune Cellular Response in Mice Inoculated with Δpgm

Figure 7:
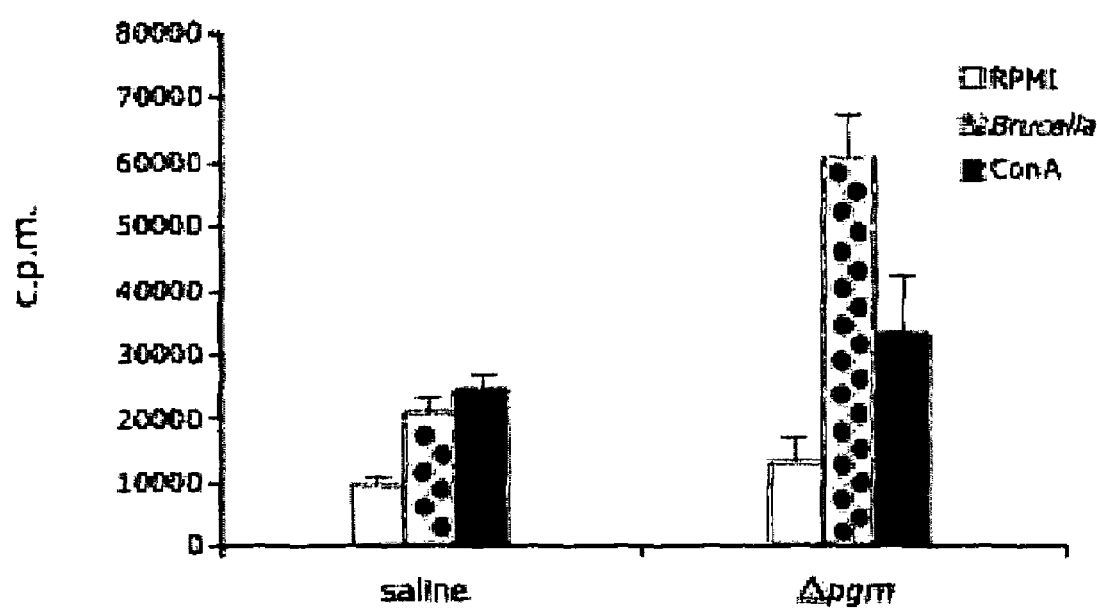
FIG. 7 is a modified bar chart representing the results obtained in a lymphocyte proliferation assay. The mice were inoculated with $10^7$ CFU of Δpgm or saline solution. Eight (8) weeks post-inoculation, the spleens were recuperated and stimulated with heat inactivated *B. abortus* S2308, RPMI medim or ConA. The bars represent the median± standard deviation of measure of the assays, which were performed four (4) times.

The lymphoproliferative response and the cytokine profile generated against the stimulation with the inactive B. abortus 2308 strain was analyzed in the spleens of the mice inoculated with the Δpgm strain or in the control group inoculated with a physiologic solution. At eight (8) weeks post-inoculation, the splenocytes recovered from mice inoculated with Δpgm proliferated in specific manner to the stimulation, in comparison to the control group which did not demonstrate this response (see FIG. 7). This lymphoproliferative response was concomitant with the secretion of high levels of gamma-interferon (IFNγ), 112.0 ng/ml versus 16.6 ng/ml in the unvaccinated control group. Interleukin 4 (IL-4) was not detected in the slenocyte resuspension obtained from both the group vaccinated with Δpgm or from the control group. These assays indicate that the Δpgm strain has the capacity to generate a classic-type Th1 cellular immune response.

Protection Capacity Assay in a Strain for the Murine Model

To analyze the protective capacity of the B. abortus Δpgm strain, protection assays were carried out using the murine model which is widely described and accepted in scientific literature as a valid model to evaluate vaccines against brucellosis.

Six week old female mice of the Balb/C strain were divided into three (3) lots A, B and C. Lot A, the unvaccinated control group, was inoculated with saline solution. Lot B vaccinated with Δpgm, was inoculated intraperitoneally with 1×10$^7$ CFU of Δpgm. Lot C control group vaccinated with S-19 was inoculated intraperitoneally with 1×10$^5$ CFU of the pathogenic B. abortus S-19 vaccine strain to compare the Δpgm's efficiency against the classic brucellosis vaccine utilized in different countries. Eight weeks after vaccination the three animal groups were challenged with 5×10$^5$ CFU of the pathogenic B. abortus 2308 strain. Two (2) and four (4) weeks after the mice were challenged, 5 animals from each lot were sacrificed, their spleens were removed, homogenized in physiologic solution and processed to evaluate the number of CFU in the pathogenic strain. The protection units were defined as the difference between the number of viable bacteria recovered in the spleens of the mice inoculated with Δpgm and those recovered from the unvaccinated control group. The efficacy of the vaccine was expressed as log$_{10}$ of the protection. The results are shown in Table 1. Δpgm generated significant protection levels at two (2) and four (4)

weeks post-challenge, with 2.25 and 1.93 units of protection, respectively. As expected, the vaccine strain B. abortus S-19 also induced significant protection at four (4) weeks post challenge (1.78 units of protection). The efficacy of the Δpgm strain was similar and comparable to that of the S-19 vaccine strain. These results indicate that Δpgm confers protection against infection by pathogenic strains of Brucella abortus, added to Δpgm's lack of capacity to generate O-antibodies, this confirms the potential of this strain for use as a vaccine against brucellosis in cattle.

TABLE 1

| Group inoculated with: (n = 5) | Median $\log_{10}$ of Brucella ± SD in spleens at days post challenge | | $\log_{10}$ of protection at days | |
|---|---|---|---|---|
| | 14 | 28 | 14 | 28 |
| Saline | 5.35 ± 0.14 | 4.73 ± 0.41 | — | — |
| Δpgm | 3.10 ± 0.37 | 2.80 ± 0.87 | $2.25^a$ | $1.93^a$ |
| S-19 | ND | 2.95 ± 0.48 | ND | $1.78^a$ |

Note:
$^a$ = $P < 0.05$ (significant) compared with the value of the control group.
ND = not determined.

Virulence Assays in Bovine

To evaluate the potential pathogenicity and/or abortigenic capacity of the B. abortus Δpgm strain in bovine, 14 young, female cows in their sixth month of pregnancy, were inoculated intravenously with $1 \times 10^9$ CFU of B. abortus Δpgm. After the inoculation and until birth, clinical signs were controlled and blood samples were taken to evaluate serologic response.

All of the animals analyzed had normal births, no abortions were detected (0/14), and none of the animals showed any clinical signs of Brucella infection. The sera of the young cows did not present serologic reversion against Brucella's LPS antigen. These results indicate that the B. abortus Δpgm strain does not present the beginnings of pathogenicity residual in bovine, data which correlates with the non-virulence of the strain in the murine model.

B. abortus Δpgm does not Induce the Formation of Agglutinant Antibodies

Due to the nature of the deletion of B. abortus Δpgm strain, the cellular wall of the mutant is severely affected by the lack of the lipopolysaccharide. This characteristic makes this B. abortus Δpgm vaccine strain incapable of inducing agglutinant antibodies, that are present in animals infected with the pathogenic or the S-19 vaccine strain. This facilitates routine serologic assays to discriminate between vaccinated and infected animals.

To demonstrate the lack of agglutinating capacity of the B. abortus Δpgm strain, 34 calves, 4 months old, previously vaccinated at 3 months of age with the B19 strain, were vaccinated subcutaneously with $1 \times 10^9$ CFU of B. abortus Δpgm. Animal blood samples were taken at 15, 30, 60, 90 and 120 days post-vaccination and submitted through classic agglutination assays in-vitro, test of the 2-ME, platelet microagglutination and BPA. None of the serum samples generated agglutination in the assays that were performed. Serum-conversion was not observed until the final period of the sampling (120 days after vaccination).

These results are consistent with the genetic characteristic of the B. abortus Δpgm strain, which indicates that the use of this strain as a new vaccine strain against bovine brucellosis would permit fast and simple determination of the sanitary status of the animals without generating confusing results when vaccinated animals must be discriminated from the infected ones.

Likewise, the vaccination assays using B. abortus Δpgm on calves previously vaccinated with the traditional B. abortus S-19 strain, indicate that the same did not suffer reinforcement of the anti-LPS antibody titers. These characteristics suggest that B. abortus Δpgm could be a useful vaccine to improve the sanitary status of herds through re-vaccination in eradication campaigns and are specially designed to reduce the incidence of infection when they are presented in epidemic growths on herds previously vaccinated with traditional strains.

Use of the Δpgm Strain to Prepare a Vaccine

New Brucella Δpgm strains described herein, preferably the B. abortus Δpgm assayed, are useful to prepare a vaccine that while being applied on an animal or man provides immunity against other wild type pathogenic Brucella strains, thus preventing the manifestation of disease symptoms.

The vaccine presents an effective quantity of the protective strain to affect an animal or man in a positive way and achieve developing immunity, this affects the course and severity of the disorders described previously that are manifested in the animals infected with the wild Brucella strain. The effectiveness of the utilized quantity will depend on the way it is administered and the corporal mass of the animal being vaccinated.

Generally, any mode of delivery that is compatible with the application of a live strain to produce an acceptable protective effect can be employed. The preferred mode of delivery is parenteral, such as subcutaneous, intramuscular or intravenous injections.

The dose to be administered will depend on the type of animal being treated, as well as its weight, age, and individual response. For example, it can be established that the active agent dose in bovines, in other words the attenuated strain, to obtain protection against brucellosis can oscillate between $10^7$ and $10^{13}$ CFU, preferably the dose of the active agent oscillates between $10^9$ and $10^{11}$ CFU.

The vaccine for this invention can be prepared according to the techniques routinely used for the preparation of brucellosis live vaccines.

The vaccine for this invention can be formulated in dosage units for their application via pre-prepared injection, where the active agent, in other words the viable, attenuated strain, is suspended for its application in a vehicle that can be diluted in a pharmaceutically acceptable agent such as isotonic saline solution.

In a different preparation, the vaccine for the present invention can be made with the lypholized active agent, of the attenuated strain, with the previous aggregate of a pharmaceutically acceptable agent to prevent freezing and consequently cellular destruction via crystallization, such as, glycerin.

Utility

Generally, Brucella Δpgm strains for the present invention, particularly the Brucella abortus Δpgm strain, possesses optimal protective activity against infection provoked by wild type pathogenic Brucella strains. Moreover, they present a low toxicity, which is also optimal in security, and do not interfere in serological assays performed to determine the level of infection. Thus, the strains for the invention can be employed to prepare vaccines that can be used as agents for the prevention of infection produced by pathogenic Brucella strains. This way, man, rodents and domestic animals will be liberated from this burden, controlling animal health, thereby benefiting farm animal health and breeding activity.

REFERENCES

Genetic engineering techniques that are described herein can be accomplished according to the methods described in the following publications:

Ausubel, F. M.; Brent, R.; Kingston, R. E.; Moore, D. D.; Seidman, J. G.; Smith, J. A. and Struhl, K. "Current protocols in molecular biology", 1987. Wiley Interscience, New York, N.Y., Volume 1.

Sambrook, J.; Fritsch, E. F. and Maniatis, T. "Molecular cloning: a laboratory manual", 1989. Cold Spring Harbor Laboratory Press, Cold Spring Harbor, N.Y.

Nielsen, K. H. and Duncan, J. R. "Animal Brucellosis", 1990. CRC Press, Inc., Boca Raton, Fla.

Young, E. J. and Corbel, M. J. "Brucellosis: Clinical and laboratory aspects", 1989. CRC Press, Inc., Boca Raton, Fla.

Comerci D. J., Pollevick G. D., Vigliocco A. M., Frasch A. C. C. and Ugalde R. A.; "Vector Development for the Expression of Foreign Proteins in the Vaccine Strain *Brucella abortus* S19"; *Infection and Immunity,* 1998. 66: 3862-3866

*Nucleic Acids Research* 13:3021-3030 (1985)

Verger J. M., Grimont F., Grimont P. A. D. and Grayon M., *Brucella*, a monospecific genus as shown by deoxyribonucleic acid hybridization; Int. J. Syst. Bacteriol., 1985; 35:292-5

What is claimed is:

1. An isolated nucleotide sequence of the pgm gene of a *Brucella* bacterium modified by a partial or complete deletion of the sequence coding for phosphoglucomutase.

2. The isolated nucleotide sequence of claim 1, wherein said *Brucella* bacterium is selected from the group consisting of *B. abortus* and *B. abortus* 2308.

3. A plasmid containing a nucleotide sequence of the pgm gene of a *Brucella* bacterium modified by a partial or complete deletion of the sequence coding for phosphoglucomutase.

4. A plasmid, pSG75, containing the dicistronic cassette SacB-Gm and having the nucleotide sequence represented by SEQ ID NO: 1.

5. A method of preparing a plasmid, pSG75, containing the dicistronic cassette SacB-Gm comprising:
   (a) excision of the SacB gene by digestion with at least one restriction enzyme having at least two recognition sites flanking the SacB gene;
   (b) isolation of the excised SacB gene;
   (c) ligation of the excised SacB gene into a recipient plasmid;
   (d) excision of the accI gene with at least one restriction enzyme having at least two recognition sites flanking the accI gene;
   (e) isolation of the excised accI gene; and
   (f) ligation of the excised accI gene into said recipient plasmid.

6. A plasmid containing the pgm gene of *Brucella* bacterium, wherein said pgm gene is interrupted by the dicistronic cassette SacB-Gm.

7. A method of preparing the plasmid of claim 6 comprising:
   (a) cleavage of the plasmid containing the dicistronic cassette SacB-Gm with at least one restriction enzyme having at least two recognition sites flanking the dicistronic cassette SacB-Gm;
   (b) isolation of the restriction enzyme cleaved fragment containing the dicistronic cassette SacB-Gm;
   (c) cleavage of the plasmid containing the pgm gene of *Brucella* with a restriction enzyme having a recognition site within the pgm gene sequence; and
   (d) ligation of the cleavage product fragment containing the dicistronic cassette SacB-Gm into the cleaved plasmid containing the pgm gene of *Brucella* bacterium.

8. An attenuated *Brucella* bacterium strain comprising a *Brucella* bacterium having a pgm gene modified by a partial or complete deletion of said pgm gene, wherein said *Brucella* bacterium is incapable of synthesizing phosphoglucomutase.

9. An attenuated *Brucella* bacterium strain as in claim 8 wherein the *Brucella* bacterium is selected from the group consisting of *B. melitensis*, *B. abortus*, *B. abortus* 2308, *B. suis*, *B. ovis*, *B. canis*, *B. neotomae*, and *B. maris*.

10. A method of generating an attenuated *Brucella* bacterium strain having a pgm gene modified by a partial or complete deletion of said pgm gene, said method comprising:
   (a) introduction of the plasmid containing the pgm gene interrupted with the dicistronic cassette SacB-Gm into a *Brucella* bacterium;
   (b) selection of an intermediary strain of *Brucella* bacterium containing the plasmid which carries the pgm gene interrupted with the dicistronic cassette SacB-Gm by virtue of the strain's ability to survive in the presence of gentamicin and kanamycin and the strain's inability to survive in the presence of sucrose;
   (c) introduction of the plasmid containing a fragment of the pgm gene of *Brucella* bacterium modified by a partial or complete deletion of the sequence coding for phosphoglucomutase into a donor bacterium;
   (d) conjugation of said donor bacterium with said intermediary strain of *Brucella* bacterium;
   (e) selection of conjugants able to survive in the presence of sucrose and unable to survive in the presence of gentamicin and kanamycin; and (f) verification that the selected conjugants lack phosphoglucomutase activity.

11. An attenuated *Brucella* bacterium strain generated by the method of claim 10 wherein said *Brucella* bacterium of method step (a) in claim 10 is selected from the group of *Brucella* bacteria consisting of *B. melitensis, B. abortus, B. abortus* 2308, *B. suis, B. ovis, B. canis, B. neotomae*, and *B. maris*.

12. A live vaccine for immunization, prophylaxis, or treatment of a mammal at risk of contracting or suffering from Brucellosis, said vaccine comprising a *Brucella* bacterium having a pgm gene modified by at least a partial deletion of said pgm gene wherein the *Brucella* bacterium is incapable of synthesizing phosphoglucomutase.

13. A vaccine as in claim 12 wherein said *Brucella* bacterium is at least one selected from the group consisting of *B. melitensis* Δpgm, *B. abortus* Δpgm, *B. abortus* 2308 Δpgm, *B. suis* Δpgm, *B. ovis* Δpgm, *B. canis* Δpgm, *B. neotomae* Δpgm and *B. maris* Δpgm.

14. A vaccine as in claim 12 wherein the *Brucella* bacterium has been transformed to express an antigenic label.

15. A vaccine as in claim 14 wherein the antigenic label comprises a highly antigenic repetitive antigen.

16. A vaccine of claim 14, wherein the antigenic label is different from the antigenic label in another lot of such vaccine, whereby animals inoculated in different geographic regions, during different vaccination periods, or with products produced by different companies, can be differentiated.

17. A vaccine as in claim 12, wherein said *Brucella* bacterium is lyophilized.

18. A method of making a live vaccine for immunization, prophylaxis, or treatment of a mammal at risk of contracting or suffering from Brucellosis, said vaccine comprising a *Brucella* bacterium having a pgm gene modified by a partial or complete deletion of said pgm gene wherein the *Brucella* bacterium is incapable of synthesizing phosphoglucomutase, comprising introducing into a *Brucella* bacterium a nucleotide sequence of the pgm gene of a *Brucella* bacterium modified by a partial or complete deletion of the sequence coding for phosphoglucomutase.

19. A method of making a live vaccine for immunization, prophylaxis, or treatment of a mammal at risk of contracting or suffering from Brucellosis, said vaccine comprising a *Brucella* bacterium having a pgm gene modified by a partial or complete deletion of said pgm gene wherein the *Brucella* bacterium is incapable of synthesizing phosphoglucomutase, comprising:

(a) introduction of the plasmid containing the pgm gene interrupted with the dicistronic cassette SacB-Gm into the *Brucella* bacterium;

(b) selection of an intermediary strain of *Brucella* bacterium containing said plasmid containing the pgm gene interrupted with the dicistronic cassette SacB-Gm by virtue of said intermediary strain's ability to survive in the presence of gentamicin and kanamycin and said intermediary strain's inability to survive in the presence of sucrose;

(c) introduction of the plasmid containing a fragment of the pgm gene of *Brucella* bacterium modified by a partial or complete deletion of the sequence coding for phosphoglucomutase into a donor bacterium;

(d) conjugation of said donor bacterium with said intermediary strain of *Brucella* bacterium;

(e) selection of conjugants able to survive in the presence of sucrose and unable to survive in the presence of gentamicin and kanamycin; and (f) verification that the resultant attenuated *Brucella* bacterium strain lacks phosphoglucomutase activity.

20. A vaccine produced by the method of claim 19 wherein the *Brucella* bacterium is selected from the group consisting of *B. melitensis, B. abortus, B. abortus* 2308, *B. suis, B. ovis, B. canis, B. neotomae*, and *B. maris*.

* * * * *

SEQUENCE LISTING

```
<160> NUMBER OF SEQ ID NOS: 3

<210> SEQ ID NO 1
<211> LENGTH: 5319
<212> TYPE: DNA
<213> ORGANISM: Dicitronic pSacB-GM vector

<400> SEQUENCE: 1
gggcgaattg ggcccgacgt cgcatgctcc cggccgccat ggcggccgcg ggaattcgat     60
gaccgctaac acagtacata aaaaaggaga catgaacgat gaacatcaaa aagtttgcaa    120
aacaagcaac agtattaacc tttactaccg cactgctggc aggaggcgca actcaagcgt    180
ttgcgaaaga aacgaaccaa aagccatata aggaaacata cggcatttcc catattacac    240
gccatgatat gctgcaaatc cctgaacagc aaaaaaatga aaaatatcaa gttcctgaat    300
tcgattcgtc cacaattaaa aatatctctt ctgcaaaagg cctggacgtt tgggacagct    360
ggccattaca aaacgctgac ggcactgtcg caaactatca cggctaccac atcgtctttg    420
cattagccgg agatcctaaa aatgcggatg acacatcgat ttacatgttc tatcaaaaag    480
tcggcgaaac ttctattgac agctggaaaa acgctggccg cgtctttaaa gacagcgaca    540
aattcgatgc aaatgattct atcctaaaag accaaacaca agaatggtca ggttcagcca    600
catttacatc tgacggaaaa atccgtttat tctacactga tttctccggt aaacattacg    660
gcaaacaaac actgacaact gcacaagtta acgtatcagc atcagacagc tctttgaaca    720
tcaacggtgt agaggattat aaatcaatct ttgacggtga cggaaaaacg tatcaaaatg    780
tacagcagtt catcgatgaa ggcaactaca gctcaggcga caaccatacg ctgagagatc    840
ctcactacgt agaagataaa ggccacaaat acttagtatt tgaagcaaac actggaactg    900
aagatggcta ccaaggcgaa gaatctttat ttaacaaagc atactatggc aaaagcacat    960
cattcttccg tcaagaaagt caaaaacttc tgcaaagcga taaaaaacgc acggctgagt   1020
tagcaaacgg cgctctcggt atgattgagc taaacgatga ttacacactg aaaaaagtga   1080
tgaaaccgct gattgcatct aacacagtaa cagatgaaat tgaacgcgcg aacgtcttta   1140
aaatgaacgg caaatggtac ctgttcactg actcccgcgg atcaaaaatg acgattgacg   1200
gcattacgtc taacgatatt tacatgcttg gttatgtttc taattcttta actggcccat   1260
acaagccgct gaacaaaact ggccttgtgt taaaaatgga tcttgatcct aacgatgtaa   1320
cctttactta ctcacacttc gctgtacctc aagcgaaagg aaacaatgtc gtgattacaa   1380
gctatatgac aaacagagga ttctacgcag acaaacaatc aacgtttgcg ccaagcttcc   1440
```

```
tgctgaacat caaaggcaag aaaacatctg ttgtcaaaga cagcatcctt gaacaaggac   1500
aattaacagt taacaaataa aaacgcaaaa gaaaatgccg atatcctatt ggcattttct   1560
tttatttctt atcaacatat cactagttag gatccttgac ataagcctgt tcggttcgta   1620
aactgtaatg caagtagcgt atgcgctcac gcaactggtc cagaaccttg accgaacgca   1680
gcggtggtaa cggcgcagtg gcggttttca tggcttgtta tgactgtttt tttgtacagt   1740
ctatgcctcg ggcatccaag cagcaagcgc gttacgccgt gggtcgatgt tgatgttat   1800 ggagcagcaa cgatgttacg cagcagcaac gatgttacgc agcagggcag tcgccctaaa   1860
acaaagttag gtggctcaag tatgggcatc attcgcacat gtaggctcgg ccctgaccaa   1920
gtcaaatcca tgcgggctgc tcttgatctt ttcggtcgtg agttcggaga cgtagccacc   1980
tactcccaac atcagccgga ctccgattac ctcgggaact tgctccgtag taagacattc   2040
atcgcgcttg ctgccttcga ccaagaagcg gttgttggcg ctctcgcggc ttacgttctg   2100
cccaggtttg agcagccgcg tagtgagatc tatatctatg atctcgcagt ctccggcgag   2160
caccggaggc agggcattgc caccgcgctc atcaatctcc tcaagcatga ggccaacgcg   2220
cttggtgctt atgtgatcta cgtgcaagca gattacggtg acgatcccgc agtggctctc   2280
tatacaaagt tgggcatacg ggaagaagtg atgcactttg tatcgaccc aagtaccgcc   2340 acctaaggat cctacccggg ctgcaggaat tcgatatcaa gcttatcgat accgtcgacc   2400
atatgggaga gctcccaacg cgttggatgc atagcttgag tattctatag tgtcacctaa   2460
atagcttggc gtaatcatgg tcatagctgt ttcctgtgtg aaattgttat ccgctcacaa   2520
ttccacacaa catacgagcc ggaagcataa agtgtaaagc ctggggtgcc taatgagtga   2580
gctaactcac attaattgcg ttgcgctcac tgcccgcttt ccagtcggga aacctgtcgt   2640
gccagctgca ttaatgaatc ggccaacgcg cggggagagg cggtttgcgt attgggcgct   2700
cttccgcttc ctcgctcact gactcgctgc gctcggtcgt tcggctgcgg cgagcggtat   2760
cagctcactc aaaggcggta atacggttat ccacagaatc aggggataac gcaggaaaga   2820
acatgtgagc aaaaggccag caaaaggcca ggaaccgtaa aaaggccgcg ttgctggcgt   2880
ttttccatag gctccgcccc cctgacgagc atcacaaaaa tcgacgctca agtcagaggt   2940
ggcgaaaccc gacaggacta taaagatacc aggcgtttcc ccctggaagc tccctcgtgc   3000
gctctcctgt tccgaccctg ccgcttaccg gatacctgtc cgcctttctc ccttcgggaa   3060
gcgtggcgct ttctcatagc tcacgctgta ggtatctcag ttcggtgtag tcgttcgct   3120 ccaagctggg ctgtgtgcac gaaccccccg ttcagcccga ccgctgcgcc ttatccggta   3180
actatcgtct tgagtccaac ccggtaagac acgacttatc gccactggca gcagccactg   3240
gtaacaggat tagcagagcg aggtatgtag gcggtgctac agagttcttg aagtggtggc   3300
ctaactacgg ctacactaga agaacagtat ttggtatctg cgctctgctg aagccagtta   3360
ccttcggaaa aagagttggt agctcttgat ccggcaaaca aaccaccgct ggtagcggtg   3420
gtttttttgt ttgcaagcag cagattacgc gcagaaaaaa aggatctcaa gaagatcctt   3480
tgatcttttc tacgggtct gacgctcagt ggaacgaaaa ctcacgttaa gggattttgg   3540
tcatgagatt atcaaaaagg atcttcacct agatcctttt aaattaaaaa tgaagtttta   3600
aatcaatcta aagtatatat gagtaaactt ggtctgacag ttaccaatgc ttaatcagtg   3660
aggcacctat ctcagcgatc tgtctatttc gttcatccat agttgcctga ctccccgtcg   3720
tgtagataac tacgatacgg gagggcttac catctggccc cagtgctgca atgataccgc   3780
```

```
gagacccacg ctcaccggct ccagatttat cagcaataaa ccagccagcc ggaagggccg        3840
agcgcagaag tggtcctgca actttatccg cctccatcca gtctattaat tgttgccggg        3900
aagctagagt aagtagttcg ccagttaata gtttgcgcaa cgttgttgcc attgctacag        3960
gcatcgtggt gtcacgctcg tcgtttggta tggcttcatt cagctccggt tcccaacgat        4020
caaggcgagt tacatgatcc cccatgttgt gcaaaaaagc ggttagctcc ttcggtcctc        4080
cgatcgttgt cagaagtaag ttggccgcag tgttatcact catggttatg gcagcactgc        4140
ataattctct tactgtcatg ccatccgtaa gatgcttttc tgtgactggt gagtactcaa        4200
ccaagtcatt ctgagaatag tgtatgcggc gaccgagttg ctcttgcccg cgtcaatac         4260 gggataatac cgcgccacat agcagaactt aaaagtgct catcattgga aaacgttctt        4320
cggggcgaaa actctcaagg atcttaccgc tgttgagatc cagttcgatg taacccactc        4380
gtgcacccaa ctgatcttca gcatctttta ctttcaccag cgtttctggg tgagcaaaaa        4440
caggaaggca aaatgccgca aaaagggaa taagggcgac acggaaatgt tgaatactca        4500
tactcttcct ttttcaatat tattgaagca tttatcaggg ttattgtctc atgagcggat        4560
acatatttga atgtatttag aaaaataaac aaatagggt tccgcgcaca tttcccccgaa        4620 aagtgccacc tgatgcggtg tgaaataccg cacagatgcg taaggagaaa ataccgcatc        4680
aggaaattgt aagcgttaat attttgttaa aattcgcgtt aaattttgt taaatcagct        4740 cattttttaa ccataggcc gaaatcggca aaatcccta taaatcaaaa gaatagaccg         4800 agataggtt gagtgttgtt ccagtttgga acaagagtcc actattaaag aacgtggact        4860
ccaacgtcaa agggcgaaaa accgtctatc agggcgatgg cccactacgt gaaccatcac        4920
cctaatcaag ttttttgggg tcgaggtgcc gtaaagcact aaatcggaac cctaaaggga       4980
gcccccgatt tagagcttga cggggaaagc cggcgaacgt ggcgagaaag gaagggaaga       5040
aagcgaaagg agcgggcgct agggcgctgg caagtgtagc ggtcacgctg cgcgtaacca       5100
ccacacccgc cgcgcttaat cgccgctac agggcgcgtc cattcgccat tcaggctgcg         5160
caactgttgg gaagggcgat cggtgcgggc ctcttcgcta ttacgccagc tggcgaaagg        5220
gggatgtgct gcaaggcgat taagttgggt aacgccaggg ttttcccagt cacgacgttg       5280
taaaacgacg gccagtgaat tgtaatacga ctcactata                              5319
```

<210> SEQ ID NO 2
<211> LENGTH: 1862
<212> TYPE: DNA
<213> ORGANISM: Brucella abortus

<400> SEQUENCE: 2

```
ctttgttatt ttcaaacaac aagtttgatc tatcttgtct tgcaatgacc gcaaacaccg          60
acaaggtgca cggtgccaac cgattgaaac gaacgggaac aacatgaccg tcaagaccat         120
tgcgaccacg ccataccagg atcaacagcc gggcacttcg ggcttgcgca agaaggttcc         180
ggttttccag cagcccaatt atgcagaaaa tttcatccag tcgatcttcg acgtgctgga         240
ggggttcaag gcaagacgc tcgtggttgg cggcgacgga cgcttttata accgcgaggt          300
gatccagaag cttatcaaga tcgcagccgc caacggtttt ggccgtatca tggtgggaca         360
gggcggcatt ctttccacgc cagccgcctc caacatgatc cgcaagtaca agccttcgg          420 tggcatgatc ctttcggcca gccacaatcc gggcgggcct acgcaggatt tcggcatcaa        480
gtacaatatc ggcaatggtg gaccggcacc cgaaaagatc accgaagcga tcttcgcccg        540
ctcaaaggtg atcgaccagt ataaaattgc agatgcagcc gatatcgaca agatcggcac        600
```

-continued aagcaagatc ggcgataccg aggtggtcat cttcgatccg gtggccgatt atgctgaatt 660
gatggaaagc ctgttcgatt tcgccgccat ccgcgccatg ataaaaggcg gcttccagat 720
gaagttcgac gccatgcatg cggtgaccgg gccttatgcc aaggaaatct tcgagcgccg 780
cctcggtgcg cccgaaggca gcgtcgtcaa tttcgtgccc ctgccggatt tcggtggcca 840
tcacccggat ccaaacctcg tctatgccaa ggatctctac gatcttctga tgtccagcca 900
tgcgccggat tttggcgccg cctccgacgg cgatggcgat cgcaacctca ttctcgggcg 960
cggtatcttc atcacgccgt cagattcgct tgccatgctg gccgcaaatg cccatctggc 1020
gccgggctat aaaggcggta tcaagggcat tgcccgttcc atgccgacga gcgccgccgc 1080
cgaccgcgtg gcggaaaaac tcggtatcgg catgtatgaa accccgaccg gctggaaatt 1140
cttcggcaat cttctcgaca gcggcaaggt gacgatctgc ggcgaggaaa gctccggcac 1200
cggctccgac catgtgcgcg aaaaagatgg tttgtgggcc gttctgctct ggctcaacat 1260
tctggcggtg cgcaaggaaa gtgtgaaggc aatcgcggac gaccattggg cacgtttcgg 1320
gcgcaattat tacactcgcc acgactatga agccgtcgat tccgatattg cgacgaagct 1380
ggtggctgac ctgcgcggca agcttgccgg cctgcccggc acgagcgtca atggcctcag 1440
gatcgaaaag gccgacgact tcgcctatca tgatcccgtt gatggctcga ccagcgaaca 1500
tcagggcatc cgcatctatt ttgaaggagg tgcgcgcatc gtgcttcgcc tgtccggtac 1560
cgggacgtca ggcgcgacca tccgcatcta tatcgaacgc tatgaagccg atcctgcaaa 1620
acataatctc gacacgcagg caacgctggc cccactgatc gacgcggctg aacagatcgc 1680
cgaagtaaaa aaacgcagcg ggcggacaga gccgtcggtg gttacttgag tagggcagta 1740
gggcagtagg gcagtagggc agtagggcag tagggcagta gggcagtagg gcagtgaaga 1800
atatggtcgc tgcggccatg cgcaaccaaa acatactccc tactccctta ttccctattc 1860
cc 1862

<210> SEQ ID NO 3
<211> LENGTH: 1631
<212> TYPE: DNA
<213> ORGANISM: Brucella suis

<400> SEQUENCE: 3
atgaccgtca agaccattgc gaccacgcca taccaggatc aacagccggg cacttcgggc 60
ttgcgcaaga aggttccggt tttccagcag cccaattatg cagaaaattt catccagtcg 120
atcttcgacg tgctggaggg gttcaagggc aagacgctcg tggttggcgg cgacggacgc 180
ttttataacc gcgaggtgat ccagaagctt atcaagatcg cagccgccaa cggttttggc 240
cgtatcatgg tgggacaggg cggcattctt tccacgccag ccgcctccaa catgatccgc 300
aagtacaaag ccttcggtgg catgatcctt tcggccagcc acaatccggg cgggcctacg 360
caggatttcg gcatcaagta caatatcggc aatggtggac cggcacccga aaagatcacc 420
gaagcgatct tcgcccgctc aaaggtgatc gaccagtata aaattgcaga tgcagccgat 480
atcgatatcg acaagatcgg cacaagcaag atcggcgata ccgaggtggt catcttcgat 540
ccggtggccg attatgctga attgatggaa agcctgttcg atttcgccgc catccgcgcc 600
atgataaaag gcggcttcca gatgaagttc gacgccatgc atgcggtgac cgggccttat 660
gccaaggaaa tcttcgagcg ccgcctcggt gcgcccgaag gcagcgtcgt caatttcgtg 720
cccctgccgg atttcggtgg ccatcacccg gatccaaacc tcgtctatgc caaggatctc 780

```
                                            -continued
tacgatcttc tgatgtccag ccatgcgccg gattttggcg ccgcctccga cggcgatggc      840
gatcgcaacc tcattctcgg gcgcggtatc ttcatcacgc cgtcagattc gcttgccatg      900
ctggccgcaa atgcccatct ggcgccgggc tataaaggcg gtatcaaggg cattgcccgt      960
tccatgccga cgagcgccgc cgccgaccgc gtggcggaaa aactcggtat cggcatgtat     1020
gaaaccccga ccggctggaa attcttcggc aatcttctcg acagcggcaa ggtgacgatc     1080
tgcggcgagg aaagctccgg caccggctcc gaccatgtgc gcgaaaaaga tggtttgtgg     1140
gccgttctgc tctggctcaa cattctggcg gtgcgcaagg aaagtgtgaa ggcaatcgcg     1200
gacgaccatt gggcacgttt cgggcgcaat tattacactc gccacgacta tgaagccgtc     1260
gattccgata ttgcgacgaa gctggtggct gacctgcgcg gcaagcttgc cggcctgccc     1320
ggcacgagcg tcaatggcct caggatcgaa aaggccgacg acttcgccta tcatgatccc     1380
gttgatggct cgaccagcga acatcagggc atccgcatct attttgaagg aggtgcgcgc     1440
atcgtgcttc gcctgtccgg taccgggacg tcaggcgcga ccatccgcat ctatatcgaa     1500
cgctatgaag ccgatcctgc aaaacataat ctcgacacgc aggcaacgct ggccccactg     1560
atcgacgcgg cggaacagat cgccgaagta aaaaaacgca gcgggcggac agagccgtcg     1620
gtggttactt g                                                          1631
```